United States Patent [19]

Igaue et al.

[11] Patent Number: 5,171,239
[45] Date of Patent: Dec. 15, 1992

[54] DISPOSABLE GARMENTS

[75] Inventors: Takamitsu Igaue; Katsuhide Kuramoto, both of Kawanoe; Hironori Nomura, Iyomishima; Tohru Sasaki, Kawanoe, all of Japan

[73] Assignee: Uni-Charm Corporation, Ehime, Japan

[21] Appl. No.: 799,297

[22] Filed: Nov. 27, 1991

Related U.S. Application Data

[63] Continuation of Ser. No. 561,000, Aug. 1, 1990, abandoned.

[30] Foreign Application Priority Data

Aug. 10, 1989 [JP] Japan ................................. 1-209203
Sep. 19, 1989 [JP] Japan ................................. 1-242711

[51] Int. Cl.$^5$ ...................... A61F 13/15; A61F 13/20
[52] U.S. Cl. ................................. 604/385.2; 604/358; 604/378
[58] Field of Search ............ 604/366, 370, 373, 385.1, 604/385.2, 358, 378

[56] References Cited

U.S. PATENT DOCUMENTS

| 4,166,464 | 9/1979 | Korpman | 604/370 X |
| 4,655,760 | 4/1987 | Morman | |
| 4,699,620 | 10/1987 | Bernardin | 604/385.2 |
| 4,701,172 | 10/1987 | Stevens | |
| 4,710,187 | 12/1987 | Boland et al. | 604/385.1 X |
| 4,731,066 | 3/1988 | Korpman | |
| 4,842,596 | 6/1989 | Kielpikowski | |
| 4,887,602 | 12/1989 | O'Leary | 604/385.2 X |
| 5,055,103 | 10/1991 | Nomura et al. | 604/385.2 |
| 5,092,861 | 3/1992 | Nomura et al. | 604/385.2 |

FOREIGN PATENT DOCUMENTS 0252413 3/1987 European Pat. Off. .

Primary Examiner—David Isabella
Assistant Examiner—Elizabeth M. Burke
Attorney, Agent, or Firm—Fred Philpitt

[57] ABSTRACT

Disposable garments such as an open-type diaper, diaper in the form of underpants or briefs or so-called infant training underpants comprising an elastic, water-permeable topsheet, an elastic water-permeable backsheet and leg- and waist-elastic members laid along both sides of a crotch zone and respective ends of front and rear zones, characterized by that an elastic barrier sheet is sandwiched between said topsheet and backsheet and intermittently bonded to at least one of the topsheet and backsheet.

1 Claim, 2 Drawing Sheets

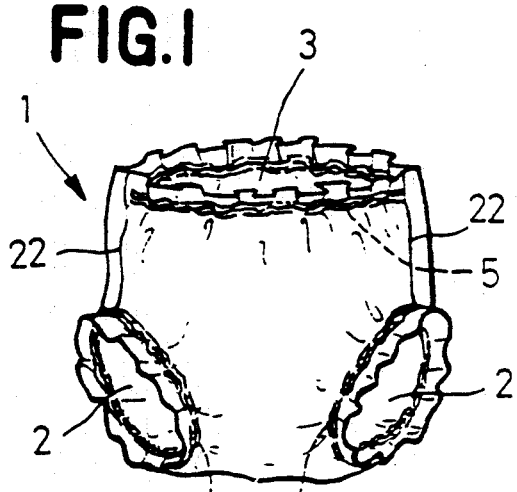
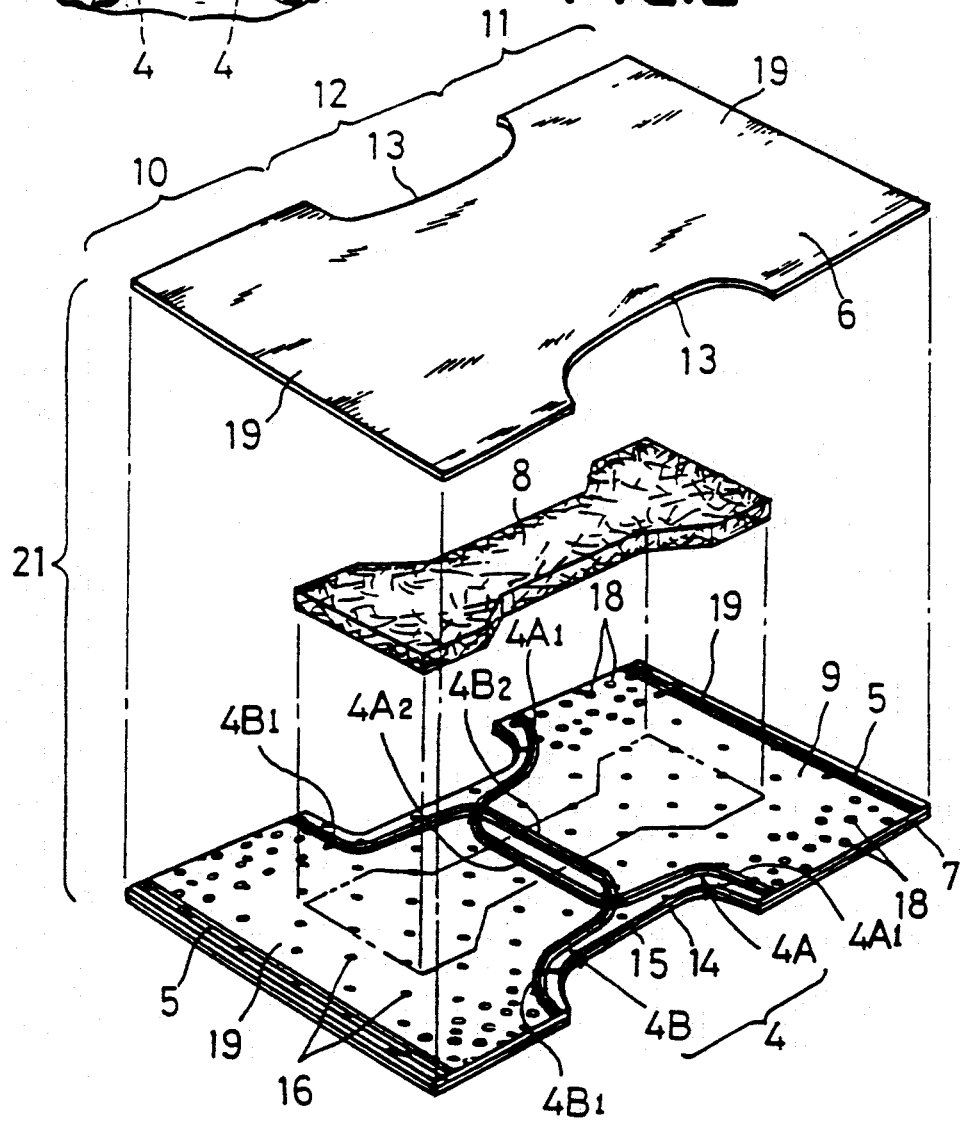

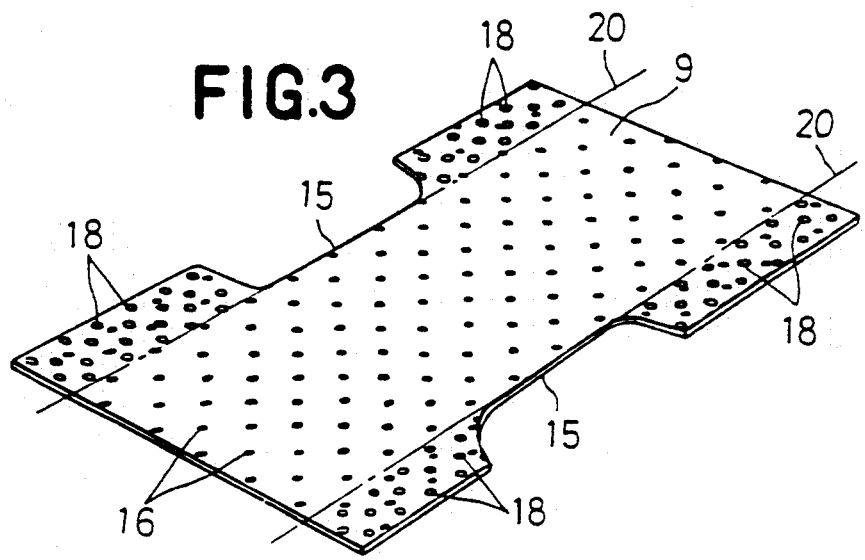
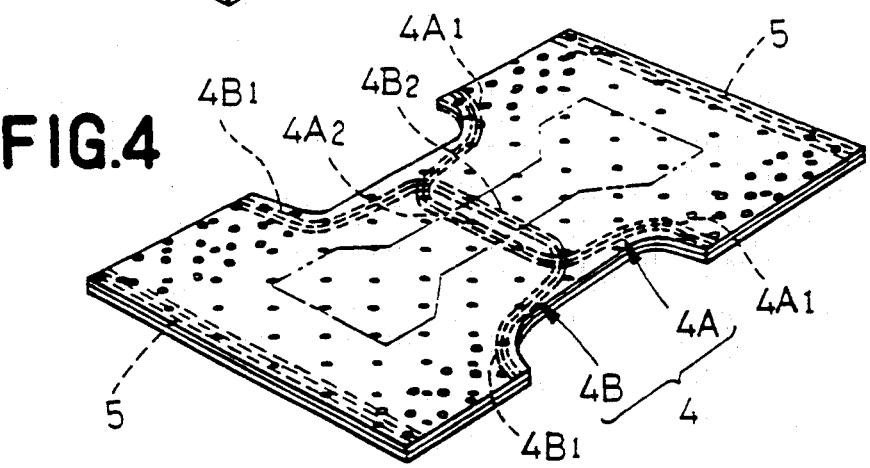
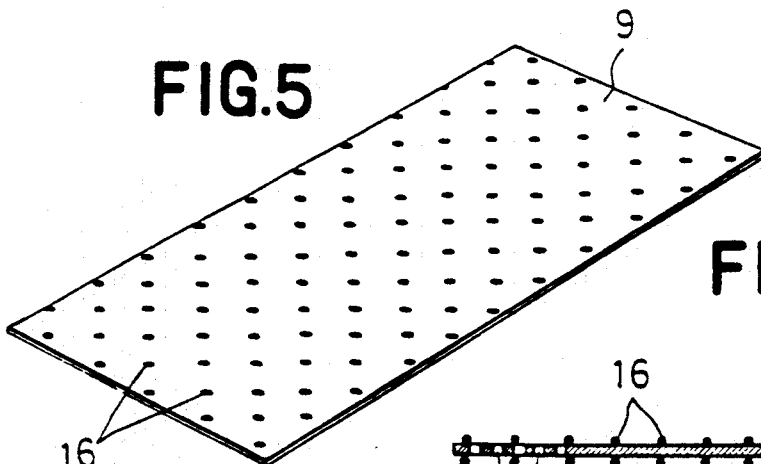
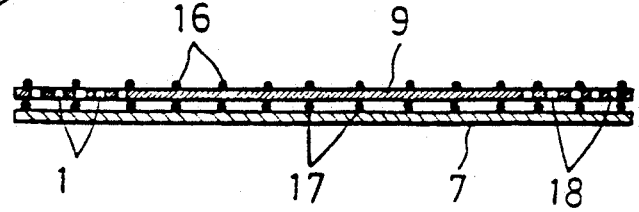

DISPOSABLE GARMENTS

This is a continuation of application Ser. No. 561,000, filed Aug. 1, 1990 now abandoned and the benefits of 35 USC 120 are claimed relative to it.

BACKGROUND OF THE INVENTION

The present invention relates to disposable garments and, more particularly, to disposable garments such as open-type diaper, diaper in the form of underpants or briefs (inclusive of diaper for incontinence) or so-called infant training underpants.

It is well known to provide such garments, for example, in the form of underpants or briefs, particularly said infant training underpants with suitable elastic members around the respective leg-openings as well as around a waist-opening and with an absorbent core sandwiched between water-permeable topsheet and backsheet.

Conventionally in such garments, both the topsheet and backsheet have not been elastic at all or, even if they are somewhat elastic, the elasticity has not been sufficient for the garments to be reliably put on the wearer's body with good fit.

In view of a fact that the topsheet and backsheet preferably should be air-permeable, these sheets have usually been made of nonwoven fabric and, as a consequence, it has been inevitable that a quantity of liquid excretion once absorbed by the absorbent core partially leaks even if the core is interposed between the sheets. Particularly in the case of infant training underpants, more or less leakage of liquid excretions might be tolerated because of the particular purpose of such underpants and for this reason the problem of leakage has often intentionally been left as it is. However, it is undesirable that a lot of liquid excretions leak immediately after occurrence of the wearer's excretions although no perfect prevention of such leakage might be required in this particular case.

A primary object of the invention is to deal with an antinomic relationship between the fact that it is preferred to use the topsheet and backsheet having good air-permeability, as it has conventionally been for disposable garments, and the fact that it is undesirable to use nonwoven fabric at least for the backsheet in order to minimize possible leakage of liquid excretions.

SUMMARY OF THE INVENTION

The object set forth above is achieved, according to the invention, by utilizing elastic nonwoven fabric for the topsheet and backsheet, interposing elastomer film as an elastic barrier sheet between the top- and backsheets and intermittently bonding the barrier sheet to at least one of the topsheet and backsheet.

When the barrier sheet is interposed between the topsheet and backsheet substantially over the entire area thereof, it is preferred to provide the barrier sheet along both sides in front and rear zones with perforations serving as air vents.

With the garments constructed according to the invention as has been mentioned above, the topsheet and backsheet as well as the barrier sheet integrally stretch and contract as the wearer's body moves. The barrier sheet apparently serves as the barrier blocking a quantity of body fluids against leaking toward the outer surface of the garments.

If the barrier sheet is provided along both sides in front and rear zones with perforations serving as air vents, the air vents will assure desired ventilation even in the case that the barrier sheet is interposed between the topsheet and backsheet substantially over the entire area thereof. If the barrier sheet is interposed between the topsheet and backsheet over an area being narrower than the area of the topsheet and backsheet but larger than the core, desired ventilation will be assured through the both side areas of the topsheet and backsheet not occupied by the barrier sheet.

If the core is sandwiched between the topsheet and backsheet, the quantity of body fluids that permeate through the topsheet is absorbed by the core.

BRIEF DESCRIPTION OF THE DRAWINGS

An embodiment of the invention is illustrated by the accompanying drawings, in which:

FIG. 1 is a perspective view showing garments of the invention;

FIG. 2 is an exploded perspective view of the components of the garment thereof;

FIG. 3 is a perspective view of a barrier sheet;

FIG. 4 is a perspective view, showing by way of example, elastic members sandwiched between a backsheet and the barrier sheet;

FIG. 5 is a perspective view showing a relatively narrow barrier sheet; and

FIG. 6 is a sectional view illustrating the manner in which the backsheet and the barrier sheet are bonded to each other.

PREFERRED EMBODIMENT OF THE INVENTION

Now the garments of the invention will be described by way of example in reference with the accompanying drawings.

Referring to FIG. 1, garments 1 have leg-openings 2 and a waist-opening 3 respectively provided with elastic members 4, 5.

Referring to FIG. 2, garments 1 comprise an elastic water-permeable topsheet 6 made of nonwoven fabric, an elastic water-permeable backsheet 7 made of the same nonwoven fabric, a mat- or sheet-like absorbent core 8, elastic members 4, 5 extending around the leg-openings and the waist-opening, respectively, and an elastic barrier sheet 9 made of elastomer film. The topsheet and backsheet 6, 7 define together with the barrier sheet 9 between their front and rear zones 10, 11 a crotch zone 12 having both side edges formed with notches 13, 14, 15. The barrier sheet 9 is bonded to the backsheet 7 over the entire area thereof by means of hot melt type adhesive or welding and the core 8 is intermittently bonded to the top surface of the barrier sheet 9 by means of hot melt type adhesive or welding. Bonding between the core 8 and the barrier sheet 9 and bonding between the topsheet 6 and the barrier sheet 9 may be achieved either by a plurality of dot-like bonding means 16 or by a plurality of intermittent lines each having a suitable length. As will be seen in FIG. 4, bonding between the backsheet 7 and the barrier sheet 9 may be also achieved by a plurality of dot-like bonding means 17 (See FIG. 6) or by a plurality of intermittent lines each having a suitable length.

It is most preferable that the core 8 is bonded not to the barrier sheet 9 but to the topsheet 6; and the core 8 and the backsheet 7 and the barrier sheet 9 are intermittently bonded to each other, respectively. In this way, elasticity of the topsheet 6, the backsheet 7 and the barrier sheet 9 can be most efficiently utilized and the hindrance of body fluid absorption by the core 8 can be avoided, which otherwise might occur due to partially floating up of the topsheet 6 from the core 8.

The barrier sheet 9 is provided along the both sides in its front and rear zones 10, 11 with fine air vents 18 (See FIG. 3). It should be understood that these air vents 18 may extend also through the top- and backsheets 6, 7.

The leg- and waist-elastic members 4, 5 are laid along the notched edges 13, 15 of the topsheet 6 and barrier sheet 9 as well as along both ends 19 of the front and rear zones 10, 11. Each of the leg-elastic members 4 comprises a first submember 4A and a second submember 4B intersecting each other at points therealong adjacent their opposite ends and their side sections 4A$_1$, 4B$_1$ extending from the respective intersecting points to the respective ends are bonded by hot melt type adhesive to the inner surface of the topsheet 6 and/or the barrier sheet 9 along the notched edges 13, 15 while their intermediate sections 4A$_2$, 4B$_2$ are positioned centrally under the core without being bonded to any of the sheets. It should be understood that these intermediate sections 4A$_2$, 4B$_2$ also may be bonded to anyone of said sheets. Each of the waist-elastic members 5 is bonded by hot melt type adhesive to the inner surface of the topsheet and/or the barrier sheet 9 along the associated end 19.

The topsheet 6 and the barrier sheet 9 may be bonded, if necessary, by heat seal ultrasonic welding or hot melt type adhesive to each other along their outer edges. The top surface of the core 8 also may be intermittently bonded to the topsheet 6, if required. As indicated by a chain line in FIG. 4, it is also possible to sandwich the elastic members 4 between the backsheet 7 and the barrier sheet 9 and, in this case, said elastic members are preferably bonded to the backsheet 7.

The barrier sheet 9 shown by FIG. 5 has a width corresponding to that defined between a pair of parallel chain lines 20 in FIG. 3, namely, the portions extending outside the respective chain lines 20 in FIG. 3 have been cut off in the embodiment of FIG. 5. With such embodiment, the ventilation is assured through the both side areas of the topsheet and backsheets that are not occupied by the barrier sheet 9.

A lamination 21 thus constructed is folded along a longitudinally middle portion and intermittently bonded together along the both side edges by heat seal or ultrasonic welding means 22 into the garments as illustrated in FIG. 1 so that these bonded side edges may be manually torn open without effort.

It should be understood that the garments of the invention may be provided in the form of well known open-type garments as final product without being subjected to the heat seal means or ultrasonic welding means 22 and in such case the rear zone 11 (See FIG. 2) will be provided along both side portions with fastener means such as the tape fastener of well known art. Sometimes there is provided no core 8, depending on particular types of garments.

The topsheet and backsheet 6, 7 may be made of nonwoven fabric which is elastic both in longitudinal and transverse directions, the core 8 may be a hot compression molded mixture of fluffy pulp, water absorptive polymer particles and hot melt type fibre, the barrier sheet 9 may be made of elastomer film being elastic both in longitudinal and transverse directions, and each of the elastic members 4, 5 may comprise at least one string or ribbon of rubber or plastic film.

Furthermore, said nonwoven fabric used as material for the topsheet and backsheet 6, 7 is obtained preferably by carding heat crimped fibre having a weight perunit area of 25 to 45 g/m$^2$ and a fineness of 0.5 to 3 d into web and heat-treating this web into a sheet. Preferred example of said heat crimped fibre is that supplied from Chisso Co., Ltd. in Japan under the trade name of "EP FIBRE".

According to the present invention, the barrier sheet interposed between the topsheet and backsheet both of which are made of elastic nonwoven fabric, serves not only to block leakage of liquid excretions but also to enhance the fit of the garment's to the wearer's body because the barrier sheet also has an elasticity and is intermittently bonded to at least one of the topsheet and backsheet so as to stretch and contract integrally with one or both of the them.

Even when the barrier sheet is sandwiched between the topsheet and backsheet over the entire area of these topsheet and backsheet, the air vents provided in the front and rear zones along the both sides of the barrier sheet will prevent the interior of the garments from becoming stuffy.

When there is provided the absorbent core, the close fit serves, in cooperation with the sealing effect provided by the leg- and waist-elastic members to further effectively block the leakage of liquid excretions.

The barrier sheet is made of elastomer film which is, unlike nonwoven fabric, substantially free from a rapidly lowered contraction stress during stretching due to loosened fibre entanglement and disjointed fibre bonding, so said barrier sheet is very effective to maintain a desired contraction stress in the entire material of the garments.

What is claimed is:

1. A disposable liquid absorbing garment comprising in combination
    (a) a liquid absorbent core (8) having a topside and a bottom side, and a perimeter,
    (b) an elastic water-permeable non-woven topsheet (6) having spaced apart side edges, said topsheet (6) being positioned against the topside of said liquid absorbent core (8) and extending outwardly beyond the perimeter of said core (8),
    (c) an elastic barrier sheet (9) that is coextensive in area with said topsheet (6) and positioned against the bottom side of said absorbent core (8), said barrier sheet (9) having two spaced apart side portions which extend laterally outwardly with respect to the perimeter of said absorbent core,
    (d) an elastic water-permeable nonwoven backsheet (7) having spaced apart side edges, said backsheet (7) being bonded to said topsheet (6) and positioned against a surface of the elastic barrier sheet (9) that is away from said absorbent core (8),
    (e) means (17) for bonding said elastic barrier sheet (9) to said backsheet (7) over the entire elastic barrier sheet (9) so that the elastic backsheet (7) and the elastic barrier sheet (9) integrally stretch and contract together as a wearer's body moves,
    (f) said elastic barrier sheet (9) being substantially coextensive in area with said backsheet (7),
    (g) a plurality of air vents (18) located in said side portions of said elastic barrier sheet (9); and
    (h) leg elastic members (4) and waist elastic members (5) disposed between said topsheet (6) and said backsheet (7),
    the combination of said topsheet (6) and backsheet (7) being folded along a longitudinally middle portion and being bonded together along portions of their side edges so as to form two spaced apart leg openings (2) on opposite sides of a folded combination resulting in a single waist opening (3), and a crotch area, wherein said leg elastic members (4) comprise
- (1) a first elastic submember (4A) that extends from one side of said folded combination to another side of said folded combination
- (2) a second elastic submember (4B) that extends from one side of said folded combination to another side of said folded combination,
- (3) said first and second elastic submembers (4A, 4B) intersecting each other at spaced apart points in said crotch area of said folded combination,
- (4) portions of said elastic submembers (4A, 4B) located between said intersecting points being unbonded to any of said sheets, and
- (5) portions of said elastic submembers (4A, 4B) that are laterally outward from said intersecting points being bonded to at least one of the topsheet (6) and the barrier sheet (9) so as to surround a leg opening.

* * * * *